(12) United States Patent
Zhang et al.

(10) Patent No.: US 11,847,934 B2
(45) Date of Patent: Dec. 19, 2023

(54) BLOOD FLOW ENVIRONMENT SIMULATION DEVICE

(71) Applicant: BEIJING BYWAVE SENSING TECHNOLOGY CO., LTD., Beijing (CN)

(72) Inventors: Lizhe Zhang, Beijing (CN); Qinhua Jin, Beijing (CN); Hao Liu, Beijing (CN); Qiaoli Zhang, Beijing (CN); Yujie Huang, Beijing (CN); Dongyun Li, Beijing (CN); Yonggang Guo, Inner Mongolia (CN)

(73) Assignee: BEIJING BYWAVE SENSING TECHNOLOGY CO., LTD., Beijing (CN)

( * ) Notice: Subject to any disclaimer, the term of this patent is extended or adjusted under 35 U.S.C. 154(b) by 371 days.

(21) Appl. No.: 17/253,938

(22) PCT Filed: Jun. 21, 2018

(86) PCT No.: PCT/CN2018/092196
§ 371 (c)(1),
(2) Date: Dec. 18, 2020

(87) PCT Pub. No.: WO2019/241962
PCT Pub. Date: Dec. 26, 2019

(65) Prior Publication Data
US 2021/0264816 A1 Aug. 26, 2021

(51) Int. Cl.
*G09B 23/30* (2006.01)
*F16K 5/04* (2006.01)
*F16K 5/12* (2006.01)

(52) U.S. Cl.
CPC .............. *G09B 23/303* (2013.01); *F16K 5/04* (2013.01); *F16K 5/12* (2013.01)

(58) Field of Classification Search
CPC ....... G09B 23/28; G09B 23/30; G09B 23/303
See application file for complete search history.

(56) References Cited

U.S. PATENT DOCUMENTS

| | | | |
|---|---|---|---|
| 7,018,327 B1 * | 3/2006 | Conti | A61M 60/148 600/16 |
| 10,937,337 B2 * | 3/2021 | Okayama | G09B 23/303 |

(Continued)

FOREIGN PATENT DOCUMENTS

| | | | | |
|---|---|---|---|---|
| CN | 101347360 A | * | 1/2009 | ............ A61M 60/00 |
| CN | 101347360 A | | 1/2009 | |

(Continued)

*Primary Examiner* — Kurt Fernstrom
(74) *Attorney, Agent, or Firm* — Scully, Scott, Murphy & Presser, P.C.

(57) ABSTRACT

A blood flow environment simulation device is disclosed, including: a liquid reservoir (1) for storing liquid; a vascular simulation tube (4); a pump (2) for pumping liquid; a plurality of circulation tubes (7, 11, 12), which form a liquid circulation path together with the vascular simulation tube; and a valve (6) located in the circulation path, having a valve inlet (17) and a valve outlet (18), wherein the area of the valve inlet (17) is variable to change the dynamic parameters of the fluid in the vascular simulation tube (4) over time. The present disclosure also relates to medical equipment that includes a blood flow environment simulation device as described.

14 Claims, 4 Drawing Sheets

(56) References Cited

U.S. PATENT DOCUMENTS

| | | | | |
|---|---|---|---|---|
| 2013/0233397 A1* | 9/2013 | McCloskey | ............ | A61F 2/2472 |
| | | | | 137/12 |
| 2014/0099617 A1* | 4/2014 | Tallman, Jr. | ............ | G09B 23/28 |
| | | | | 434/262 |
| 2015/0161347 A1* | 6/2015 | Christiansen | .......... | G16H 50/50 |
| | | | | 703/11 |
| 2017/0076635 A1* | 3/2017 | Homich | ................ | G09B 23/285 |
| 2017/0186341 A1 | 6/2017 | Sweeney | | |

FOREIGN PATENT DOCUMENTS

| | | | | | |
|---|---|---|---|---|---|
| CN | 201836432 U | * | 5/2011 | | |
| CN | 201836432 U | | 5/2011 | | |
| CN | 205302799 U | | 6/2016 | | |
| CN | 107527543 A | | 12/2017 | | |
| JP | 2015-105958 A | | 6/2015 | | |
| WO | WO-2012002334 A1 | * | 1/2012 | ............ | A61M 60/00 |
| WO | WO-2017165969 A1 | * | 10/2017 | | |

\* cited by examiner

BLOOD FLOW ENVIRONMENT SIMULATION DEVICE

CROSS-REFERENCE TO RELATED APPLICATIONS

This application is a national phase entry of PCT International Application No. PCT/CN2018/092196, filed on Jun. 21, 2018. The disclosure of PCT International Application No. PCT/CN2018/092196 is incorporated by reference herein.

TECHNICAL FIELD

The disclosure belongs to the technical field of medical devices, and specifically relates to a blood flow environment simulation device.

BACKGROUND

Interventional blood flow parameter measurement equipment, equipment used in vascular interventional surgery or the like usually need to be tested before mass production or before use. For example, a medical pressure guide wire used for minimally invasive interventional diagnosis and treatment may require a series of tests before use to ensure that the performance parameters of the pressure guide wire meet certain standards. Although there are measurement devices or systems for these interventional measurement equipment or surgical equipment, it is more desirable to provide an environment close to the real human vascular environment so as to conduct such testing experiments, in order to better check out the indicators of measurement of internal parameters of blood vessels by these equipment, such as accuracy and real-time followability.

In addition, it is desired to provide a simulation training operating platform for various vascular interventional operations to simulate the vascular environment encountered during vascular interventional diagnosis and treatment. The use of high-profile simulation environment for simulation training before a formal operation can significantly improve the technical level and operational proficiency of the operator, shorten the operation time, and ensure the success rate of the operation.

However, devices that meet the above requirements do not exist at present.

SUMMARY

To address the above-mentioned problems and requirements, this solution proposes a blood flow environment simulation device that can meet the technical objectives described in the section of BACKGROUND. The blood flow environment simulation device achieves the above technical objectives and bring other technical effects by adopting the following technical features.

The present disclosure first proposes a blood flow environment simulation device, including: a liquid reservoir for storing liquid; a vascular simulation tube; a pump for pumping liquid; a plurality of circulation tubes, which form a liquid circulation path together with the vascular simulation tube; and a valve located in the circulation path, having a valve inlet and a valve outlet, wherein the area of the valve inlet is variable to change the dynamic parameters of the fluid in the vascular simulation tube over time.

According to the above features, the liquid reservoir, the plurality of circulation tubes and the vascular simulation tube constitute a circulation path for the liquid pumped by the pump so that the liquid circulates within the circulation path. Specifically, the liquid may flow from the liquid reservoir to the vascular simulation tube, and then flow back to the liquid reservoir from the vascular simulation tube via the plurality of circulation tubes. The vascular simulation tube is able to simulate the shape and distribution of blood vessels in a specific part, including but not limited to coronary artery and carotid artery. Therefore it provides a simulation platform close to the human vascular environment for equipment testing or pre-operative simulation training. Specifically, the present disclosure simulates the heartbeats by means of the change of the area of the valve inlet. That is, the dynamic parameters of the fluid in the vascular simulation tube (flow speed, flow rate, pressure distribution or the like) are changed by the change of the area of the valve inlet, so as to simulate the changes over time of blood flow parameters (such as blood flow speed, blood pressure distribution or the like) in the blood vessel caused by the heartbeats in a realistic enough way, without the need to design a complicated device to reproduce the heart movement. It also achieves structural simplification and cost savings at the same time of ensuring its performance.

According to a preferred embodiment, the valve includes: a valve body having a valve body inlet; a valve core, which is rotatably or slidably arranged in the valve body, having a valve core inlet, a valve core cavity and a valve core outlet; wherein the overlapping portion of the valve body inlet and the valve core inlet constitutes the valve inlet, and the valve core outlet at least partially forms the valve outlet; and wherein as the valve core rotates or slides, the area of the overlapping portion of the valve body inlet and the valve core inlet changes.

According to the above features, the overlapping portion of the valve body inlet and the valve core inlet constitutes the valve inlet. By rotating or sliding the valve core, the area of the overlapping portion of the valve body inlet and the valve core inlet will change, that is, the area of the valve inlet will change. In this way, there is no need to set up a complicated mechanical structure that simulates the systolic and diastolic motion of the heart. The change of hemodynamic parameters caused by the heart motion is realized by virtue of the change of the area of the overlapping portion of the inlets. At the same time, the simple rotation or sliding movement of the valve core simulates the periodic feature of the heart movement, thereby achieving simplification of the structure and operational stability.

According to a preferred embodiment, the valve core inlet is one or more openings formed on the side wall.

According to the above features, by forming the valve core inlet on the side wall, it is easy for the valve core inlet and the valve body inlet to form an overlapping portion. And the size of the overlapping portion is easy to be controlled to change with the rotation of the valve core. With such a structure, it is easy to manufacture valve core inlets of different shapes. The change of the overlapping portion over time can be controlled by a valve core inlet of a specific shape, so as to better simulate the changes of blood flow parameters in real blood vessels.

According to a preferred embodiment, the valve core inlet is one or more cross-shaped openings formed on a side wall.

According to a preferred embodiment, the valve core inlets are two cross-shaped openings formed on the side wall and opposite to each other.

According to a preferred embodiment, the valve core inlet is one or more streamlined openings formed on the side wall.

According to the shape and position characteristics of the opening, it is possible to more realistically reproduce the change of hemodynamic parameters in the vascular simulation tube caused by heart movement.

According to a preferred embodiment, the valve core is of a hollow structure that has a closed end and an open end, and the open end at least partially forms the valve core outlet.

According to the above features, the valve core has a simple structure and is easy to manufacture and assemble.

According to a preferred embodiment, the valve is located downstream of the vascular simulation tube.

According to the above features, as the valve core rotates, the valve may cause the blood flow parameters of the vascular simulation tube upstream of the valve to change.

According to a preferred embodiment, it also includes a simulated blockage block arranged in the vascular simulation tube.

According to the above features, for example, the real environment inside the blood vessel when the blood vessel is blocked can be simulated in a good way, so as to better test the blood flow parameter measurement equipment and vascular interventional operation equipment, or so as to be used as a simulation training operation platform for the vascular interventional operation for blockage symptoms. At the same time, the operator can easily select the size, shape, and position of the blockage block according to the specific situation, so that the device has a wider range of application.

According to a preferred embodiment, it also includes an entrance for a diagnosis and treatment device downstream of the vascular simulation tube.

According to a preferred embodiment, the entrance for a diagnosis and treatment device is formed by a three-way joint.

According to the above features, the device has a reasonable and simplified structure.

According to a preferred embodiment, it also includes a heating device upstream of the vascular simulation tube.

According to the above features, the temperature of the fluid in each tube of the blood flow environment simulation device can be adjusted by the heating device, especially the temperature of the liquid in the vascular simulation tube may be accurately adjust, so as to obtain a more realistic simulation environment.

According to a preferred embodiment, it further includes a measuring device, which is at least one of the following: a temperature sensor, a pressure sensor, a flow speed sensor, and a flow rate sensor.

According to the above features, they constitute a blood flow measuring and/or feedback component, which can adjust the parameters of the blood flow environment simulation device according to the measurements provided by the temperature sensor, pressure sensor, flow speed sensor and/or flow rate sensor, thereby adjusting the parameters of the liquid in the vascular simulation tube, including but not limited to temperature, pressure, flow rate, flow speed and other parameters.

According to a preferred embodiment, it further includes a motor for rotating or sliding the valve core.

According to the above features, the rotation or sliding of the valve core may be driven and controlled by the motor, so as to realize the change of fluid dynamic parameters in the vascular simulation tube.

According to a preferred embodiment, the vascular simulation tube is connected with circulation tubes through connectors.

According to the above features, the vascular simulation tube becomes a relatively independent vascular simulation module from the entire blood flow environment simulation device. It may be easily replaced with vascular simulation modules having vascular simulation tubes of different shapes, for example, replacing the vascular simulation module having a coronary artery simulation tube with the vascular simulation module having a carotid artery simulation tube. Therefore the applications of the present disclosure are conveniently expanded by a simplified structure.

According to a preferred embodiment, the dynamic parameters include at least one of the following: flow speed, flow rate, and pressure.

According to a preferred embodiment, the liquid is water or blood.

The present disclosure also proposes to medical equipment that includes a blood flow environment simulation device according to any one of the previous claims.

Hereinafter, preferred embodiments for implementing the present disclosure will be described in more detail with reference to the accompanying drawings, so that the features and advantages of the present disclosure can be easily understood.

BRIEF DESCRIPTION OF THE DRAWINGS

In order to explain the technical solutions of the embodiments of the present disclosure more clearly, the drawings of the embodiments thereof will be briefly described below. Among them, the drawings are simply intended to illustrate some embodiments of the present disclosure, rather than limiting all the embodiments thereof to this.

DETAILED DESCRIPTION

Figure 1:
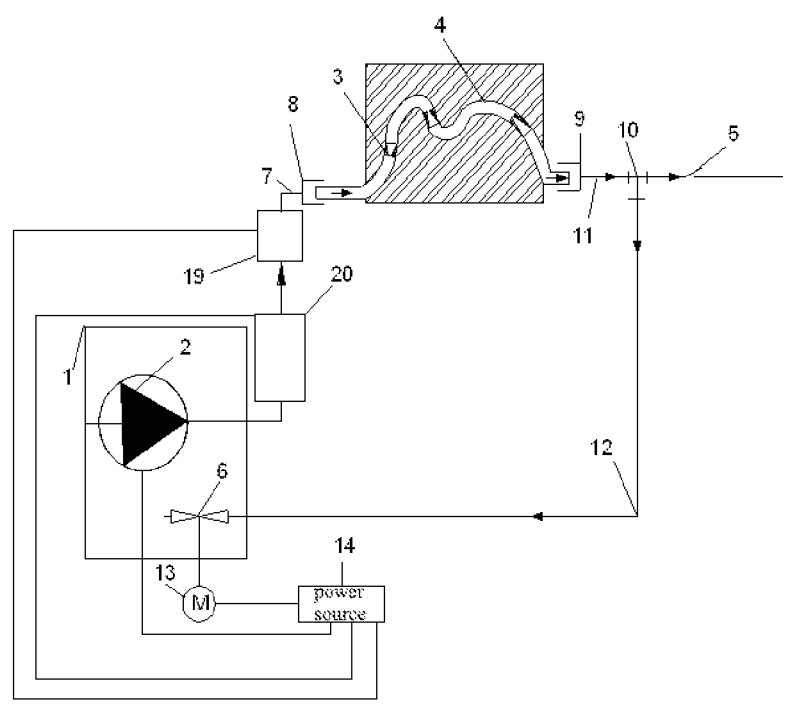
FIG. 1 shows an exemplary embodiment of a blood flow environment simulation device proposed by the present disclosure.

In order to make the objectives, technical solutions and advantages of the technical solutions of the present disclosure more clear, the technical solutions of the embodiments thereof will be described clearly and completely in the following with reference to the drawings of the specific embodiments of the present disclosure. The same reference numerals in the drawings represent the same components. It should be noted that the described embodiments are part of the embodiments of the present disclosure, but not all of them. Based on the described embodiments of the present disclosure, all the other embodiments obtained by those skilled in the art without creative efforts fall within the protection scope of the present disclosure.

The blood flow environment simulation device proposed by the present disclosure aims to simulate a real blood vessel/blood flow environment for various purposes. For example, the blood flow environment simulation device of the present disclosure may be used for testing of blood flow parameter measurement equipment and vascular interventional surgery equipment, such as testing of medical pressure guide wires. The blood flow environment simulation device may also be used as a pre-operative simulation training platform for vascular interventional surgery, including but not limited to the intervention or implantation simulation of guide wires, catheters, stent, balloons or the like. In addition to the above, it may also be used in any other situations that requires simulation of the real blood vessel/blood flow environment. At the same time, the blood flow environment simulation device is particularly suitable for the simulation of coronary arteries, for example, the testing of coronary artery blood flow parameter measurement equipment and coronary artery surgery equipment, or the simulation training platform for coronary artery surgery.

Referring to the exemplary embodiment shown in FIG. 1, the blood flow environment simulation device provided by the present disclosure includes a liquid reservoir 1 for storing liquid. The liquid may be water, blood, or other liquids that may be used to circulate in the blood flow environment simulation device.

The blood flow environment simulation device also includes a vascular simulation tube 4. The vascular simulation tube 4 is able to simulate the shape and distribution of blood vessels in a specific part, including but not limited to the shape of coronary artery, carotid artery. Therefore it provides a simulation platform close to the human vascular environment for equipment testing or pre-operative simulation training.

According to a preferred embodiment, the vascular simulation tube 4 is connected with circulation tubes through connectors 8, 9 so that the vascular simulation tube becomes a relatively independent vascular simulation module from the entire blood flow environment simulation device. Preferably, the connectors 8, 9 are connectors that are easy to disassemble, such as quick connectors, so as to facilitate disassembly and replacement of vascular simulation modules with vascular simulation tubes of different shapes, for example, replacing the vascular simulation module having a coronary artery simulation tube with the vascular simulation module having a carotid artery simulation tube.

According to a preferred embodiment, it also includes a simulated blockage block 3 arranged in the vascular simulation tube 4. The simulated blockage block 3 is used to simulate the blockage in the blood vessel. Simulated blockage blocks of different specifications may be customized according to specific requirements, and the position of the simulated blockage blocks in the vascular simulation tube may be determined according to the specific requirements.

The blood flow environment simulation device also includes a pump 2 for pumping liquid. Specifically, the liquid flows from the liquid reservoir 1 to the vascular simulation tube under the action of the pump, and then flows back to the liquid reservoir. In the embodiment as shown in FIG. 1, the pump 2 is supplied by a power source 14. The power source 14 may be an internal control power source incorporated into the blood flow environment simulation device, or may be an external power source independent of the blood flow environment simulation device.

The blood flow environment simulation device also includes a plurality of circulation tubes, which form a liquid circulation path together with the vascular simulation tube. FIG. 1 shows a first tube 7, a second tube 11, and a third tube 12. The first tube 7 is used to connect the pump 2 with the vascular simulation tube 4, and a heating device 19 and one or more blood flow analysis components 20 are provided on the first tube 7. The second tube 11 is used to connect the vascular simulation tube with a three-way joint 10. The third tube 12 is used to connect the three-way joint 10 with a valve 6. However, it shall be understood that the blood flow environment simulation device may include more or fewer circulation tubes than those shown in FIG. 1. The present disclosure does not limit the specific number and structure of the circulation tubes, as long as the circulation tubes and the vascular simulation tube form the circulation path of the liquid together. In the embodiment as shown in FIG. 1, under the action of the pump 2, the liquid sequentially passes through the liquid reservoir 1, the pump 2, the measuring device 20, the heating device 19, the vascular simulation tube 4, the valve 6 and circulates back to the liquid reservoir 1. It should be noted that FIG. 1 merely shows an exemplary embodiment, and the specific arrangement of the components is not limited to this.

The blood flow environment simulation device includes a valve 6 having a valve inlet 17 and a valve outlet 18. The area of the valve inlet 17 is variable to change the dynamic parameters of the fluid in the vascular simulation tube 4. Here, the valve inlet 17 is the entry inlet of the valve 6 that allows liquid to enter the valve, and the area of the valve inlet 17 is the area of the entry inlet, that is, the cross-sectional area of the valve inlet in a plane substantially perpendicular to the direction of liquid flow. The present disclosure simulates the heartbeats by means of the change of the area of the valve inlet. That is, the dynamic parameters of the fluid in the vascular simulation tube 4 (which includes at least one of the following: flow speed, flow rate, pressure distribution or the like) are changed by the change of the area of the valve inlet, so as to simulate the changes over time of blood flow parameters (such as blood flow speed, blood pressure distribution or the like) in the blood vessel caused by the heartbeats in a realistic enough way, without the need to design a complicated device to reproduce the heart movement.

Figure 2:
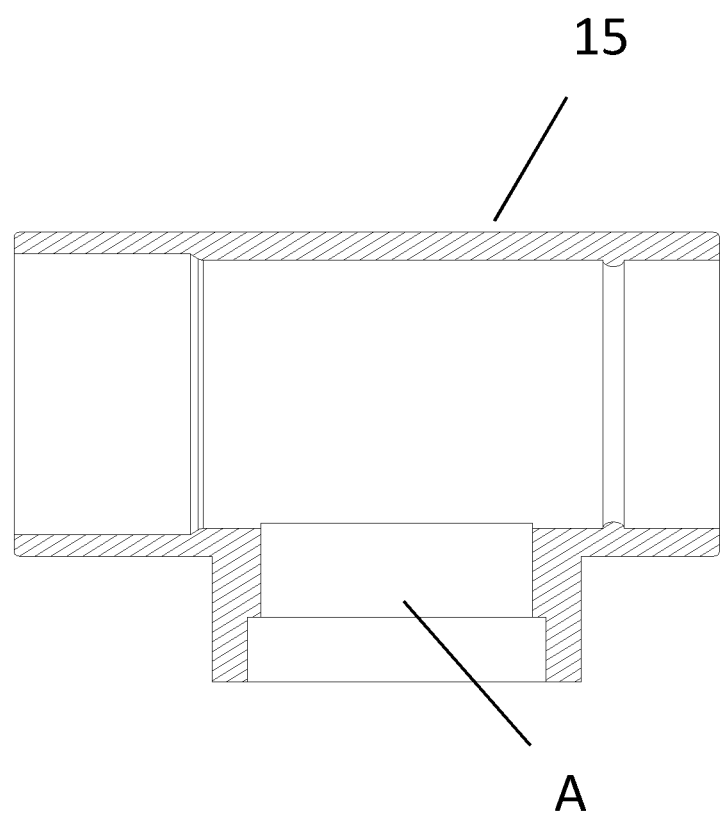
FIG. 2 shows an exemplary embodiment of a valve body.
Figure 3:
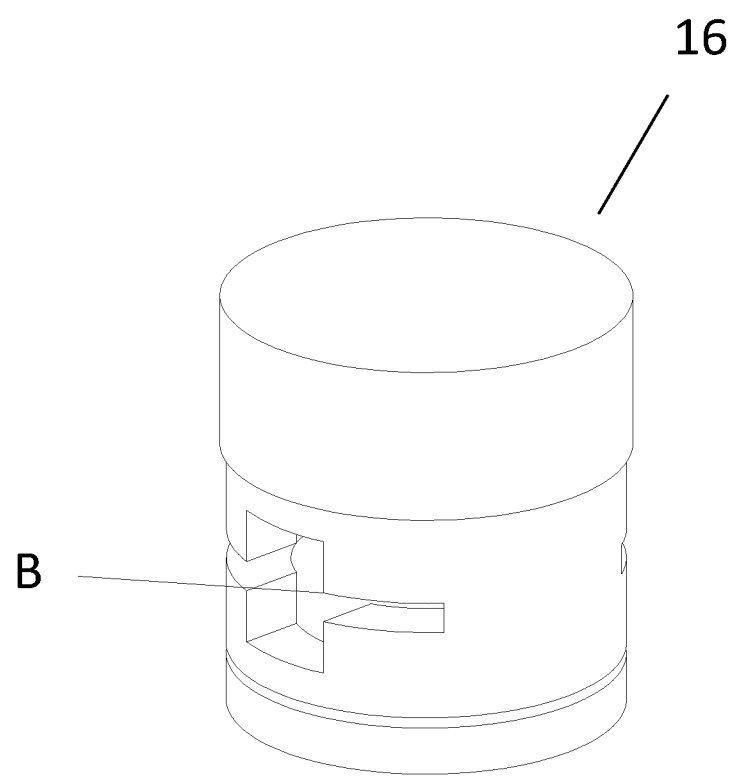
FIG. 3 shows an exemplary embodiment of a valve core.
Figure 4:
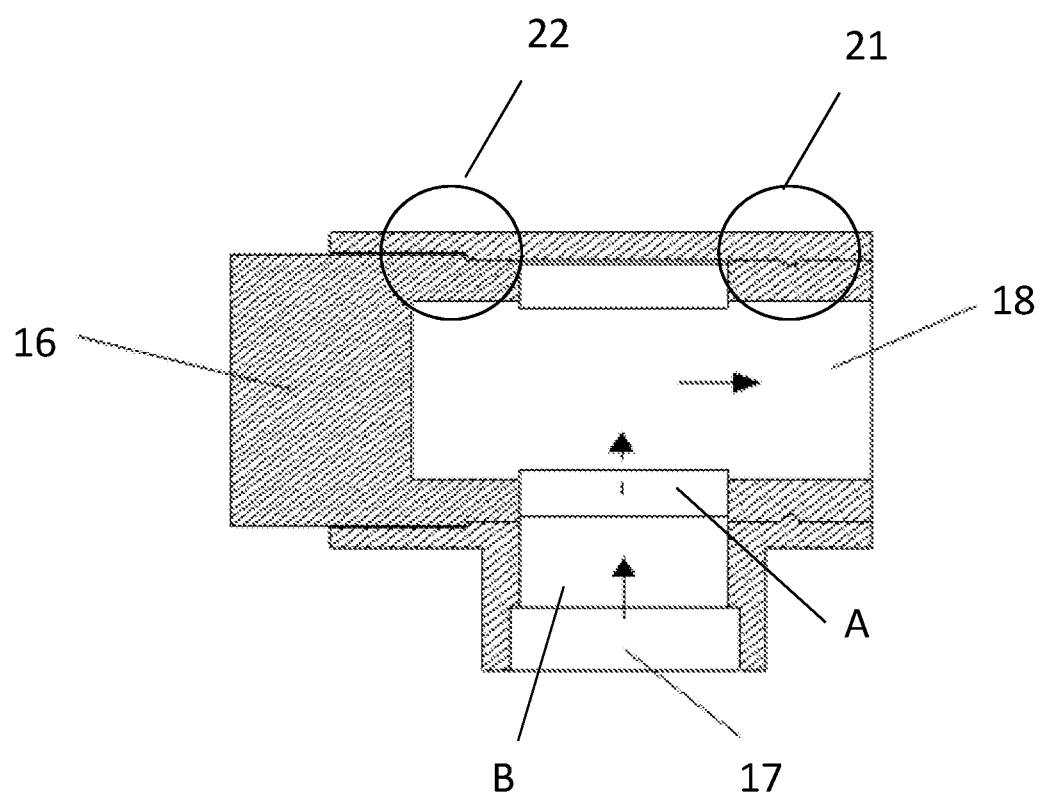
FIG. 4 shows an exemplary embodiment of a valve structure.

According to a preferred embodiment, The valve includes a valve body 15 and a valve core 16. FIG. 2 shows an exemplary embodiment of the valve body 15; FIG. 3 shows an exemplary embodiment of the valve core 16; and FIG. 4 shows a cross-sectional view of the valve core shown in FIG. 3 mounted in the valve body shown in FIG. 2. As shown by the arrow in FIG. 4, the liquid enters from the valve inlet 17 of the valve 6 and exits through the valve outlet 18 of the valve 6. The valve inlet 17 is defined by the overlapping portion of the valve body inlet A and the valve core inlet B. The valve outlet 18 is at least partially defined by the valve core outlet. For example, the valve outlet 18 may be defined only by the valve core outlet, or by the valve core outlet and a part of the valve body jointly.

As shown in FIG. 2, The valve body 15 may be roughly shaped as a three-way tube, having two opposite openings along the longitudinal axis, and an opening extending from a side wall, that is, the valve body inlet A. As shown in FIG. 3, the valve core 16 has a closed end and an open end, and the open end at least partially forms the valve outlet of the entire valve 6. The valve core inlet B is one or more openings formed on its side wall. For example, it(they) may be one or more cross-shaped openings or streamlined openings, or it(they) may be two cross-shaped openings or two streamlined openings that are opposite to each other. Term "streamlined" in this context means an opening mainly composed of smooth curves. The valve core inlet may also be formed into a quadrilateral, polygonal, or arbitrary curved shape.

As shown in FIG. 4, the valve core 16 is rotatably arranged in the valve body 15. The overlapping portion of the valve body inlet A and the valve core inlet B constitutes the valve inlet 17. As the valve core rotates, the area of the overlapping portion of the valve body inlet A and the spool inlet B gradually changes, so that the valve inlet 17 performs a cycle of being closed-half opened-fully opened-half opened-closed, thereby making parameters of the liquid in the circulation tube change periodically. At the same time, by setting the shape of the valve core inlet B, such as the cross shape described above, the periodic changes of blood flow parameters caused by heart movement can be simulated.

Although the embodiment of the drawings merely shows the embodiment in which the valve core 16 is rotatably arranged in the valve body 15, the valve core 16 may also be slidably arranged in the valve body 15. With the translation of the valve core relative to the valve body, the area of the overlapping portion of the valve body inlet A and the valve core inlet B changes, so that the parameters of the liquid in the circulation tube change periodically.

As shown in FIG. 4, the valve body 15 and the valve core 16 may have snapping portions 21 and positioning portions 22. The snapping portions 21 may be formed by an annular protrusion in the valve body 15 and a corresponding annular recess in the valve core 16. The snapping portions 21 allow the valve body 15 and the valve core 16 to be rotatably fixed together. The positioning portions 22 are formed by the respective shoulders of the valve body 15 and the valve core 16 to define their positions in the axial direction. In addition, due to the presence of the positioning portions 22, the valve body 15 forms a stepped portion open towards the outside, so that the valve core 16 can be easily inserted into the valve body 15.

According to a preferred embodiment, the valve 16 is located downstream of the vascular simulation tube 4. In this way, as the valve core rotates, the valve may cause the blood flow parameters of the vascular simulation tube upstream of the valve to change.

According to a preferred embodiment, the blood flow environment simulation device also includes an entrance for a diagnosis and treatment device downstream of the vascular simulation tube 4. According to a preferred embodiment, The entrance for the diagnosis and treatment device is formed by the three-way joint 10. Specifically, two ports of the three-way joint 10 are respectively inserted into the circulation path of the blood flow environment simulation device, and the last port forms the entrance for the diagnosis and treatment device. In the embodiment as shown in FIG. 1, Two ports of the three-way joint 10 are respectively used to connect the second tube 11 and the third tube 12 to form a circulation loop, and the last port forms the entrance for the diagnosis and treatment device.

According to a preferred embodiment, It also includes a guide wire entrance switch 5, which controllably closes and opens the entrance for the diagnosis and treatment device.

According to a preferred embodiment, the blood flow environment simulation device also includes the heating device 19 upstream of the vascular simulation tube 4. The heating device 19 may be, for example, an electric heating tube, an electric heating wire, or the like. The heating device 19 constitutes a temperature control unit, which can adjust the temperature of the fluid in each tube of the blood flow environment simulation device, especially accurately adjust the temperature of the liquid in the vascular simulation tube, so as to obtain a more realistic simulation environment.

According to a preferred embodiment, the blood flow environment simulation device further includes a measuring device 20, which may be at least one of the following: a temperature sensor, a pressure sensor, a flow speed sensor, and a flow rate sensor. These measuring devices constitute a blood flow test and feedback component, which can adjust the parameters of the blood flow environment simulation device according to the measurements provided by the temperature sensor, pressure sensor, flow speed sensor and/or flow rate sensor, thereby adjusting the parameters of the liquid in the vascular simulation tube, including but not limited to temperature, pressure, flow rate, flow speed and other parameters. Although the measuring device 20 shown in FIG. 1 is located between the pump 2 and the heating device, the measuring device 20 may also be arranged in other positions.

According to a preferred embodiment, the blood flow environment simulation device further includes a motor 13 for rotating the valve core. The valve 6 may be connected with the motor 13. Optionally, a motor connecting shaft is connected with a closed end of the valve core, so that the motor 13 drives the valve core in rotation through the motor connecting shaft 16. With the rotation speed of the motor 13, the rotation or translation speed of the valve core of the valve 6 can be altered so as to change the area of the valve inlet, thereby changing the change frequency of the dynamic parameters of the liquid. In this way, the heart rate and heart rate changes can be simulated by the rotation speed of the motor 13. The motor may be powered by the power source 14 described above.

The present disclosure also proposes to medical equipment that may include a blood flow environment simulation device according to any one of the previous claims, and may include other components such as blood flow parameter analysis instruments.

It should be noted that the drawings merely show the possible embodiments of the blood flow environment simulation device of the present disclosure, and the scope of present disclosure does not limit to them.

Unless otherwise defined, the technical or scientific terms used herein shall be construed as the ordinary meaning understood by those with ordinary skills in the field to which the present disclosure belongs. The terms "first", "second" and similar words used in the description and claims of this disclosure do not indicate any order, quantity or priority, but are only intended to distinguish different components. Similarly, words such as "a" or "one" do not necessarily mean quantity limitation. Words such as "including", "comprising" or the like mean that the elements or objects appearing before the word encompass the elements or objects listed after the word and their equivalents, but do not exclude other elements or objects. Words such as "connected", "joined" or the like are not limited to physical or mechanical connections, but may include electrical connections, whether direct or indirect. "Up", "down", "left", "right", etc. are merely intended to indicate the relative positional relationship; when the absolute position of the described object changes, the relative positional relationship may also change accordingly.

The exemplary implementations of the water pump proposed by the present disclosure have been described in detail above with reference to preferred embodiments. However, those skilled in the art can understand that the above specific embodiments can be implemented to make various changes and modifications without departing from the concept of the present disclosure, and various technical features and structures proposed in the present disclosure can be combined in various ways without going beyond the protection scope of the present disclosure, which is determined by the appended claims.

LIST OF REFERENCE NUMBERS 1 liquid reservoir
2 pump
3 simulated blockage block
4 vascular simulation tube
5 guide wire entrance switch 6 valve
7 first tube
8 connector
9 connector
10 three-way joint
11 second tube
12 third tube
13 motor
14 power source
15 valve body
16 valve core
17 valve inlet
18 valve outlet
19 heating device
20 measuring device
21 snapping portion
22 positioning portion
A valve body inlet
B valve core inlet

What is claimed is:

1. A blood flow environment simulation device, comprising:
    a liquid reservoir (1) for storing liquid;
    a vascular simulation tube (4);
    a pump (2) for pumping liquid;
    a plurality of circulation tubes (7, 11, 12), which form a circulation path for the liquid together with the vascular simulation tube; and
    a valve (6) located in the circulation path, wherein the valve (6) comprises:
        a valve body (15) having a valve body inlet (A);
        a valve core (16), rotatably or slidably arranged in the valve body (15), and having a valve core inlet (B), a valve core cavity and a valve core outlet,
        wherein the overlapping portion of the valve body inlet (A) and the valve core inlet (B) constitutes said valve inlet (17), and the valve core outlet at least partially forms said valve outlet (18);
        wherein the area of the overlapping portion of the valve body inlet (A) and the valve core inlet (B) changes as the valve core (16) rotates or slides, such that the area of the valve inlet (17) changes, to change the dynamic parameters of the fluid in the vascular simulation tube (4) over time; and
        wherein the valve core inlet (B) is one or more cross-shaped openings formed on the side wall.

2. The blood flow environment simulation device according to claim 1, wherein the valve core inlets (B) are two cross-shaped openings formed on the side wall and opposite to each other.

3. The blood flow environment simulation device according to claim 1, wherein the valve core (16) is of a hollow structure that has a closed end and an open end, and the open end forms the valve core outlet.

4. The blood flow environment simulation device according to claim 1, wherein the valve (16) is located downstream of the vascular simulation tube (4).

5. The blood flow environment simulation device according to claim 1 further including a simulated blockage block (3) arranged in the vascular simulation tube (4).

6. The blood flow environment simulation device according to claim 1 further including an entrance for a diagnosis and treatment device downstream of the vascular simulation tube (4).

7. The blood flow environment simulation device according to claim 6, wherein the entrance for a diagnosis and treatment device is formed by a three-way joint (10).

8. The blood flow environment simulation device according to claim 1 further including a heating device (19) upstream of the vascular simulation tube (4).

9. The blood flow environment simulation device according to claim 1 further including a measuring device (20), which is at least one of the following: a temperature sensor, a pressure sensor, a flow speed sensor, and a flow rate sensor.

10. The blood flow environment simulation device according to claim 1 further including a motor (13) for rotating or sliding the valve core (16).

11. The blood flow environment simulation device according to claim 1, wherein the vascular simulation tube (4) is connected with the circulation tubes by connectors (8, 9).

12. The blood flow environment simulation device according to claim 1, wherein the dynamic parameters include at least one of the following: flow speed, flow rate, and pressure.

13. The blood flow environment simulation device according to claim 1, wherein the liquid is water or blood.

14. Medical equipment that includes a blood flow environment simulation device which comprises:
    a liquid reservoir (1) for storing liquid;
    a vascular simulation tube (4);
    a pump (2) for pumping liquid;
    a plurality of circulation tubes (7, 11, 12), which form a circulation path for the liquid together with the vascular simulation tube; and
    a valve (6) located in the circulation path, wherein the valve (6) comprises:
        a valve body (15) having a valve body inlet (A); and
        a valve core (16), rotatably or slidably arranged in the valve body (15), and having a valve core inlet (B), a valve core cavity and a valve core outlet;
        wherein the overlapping portion of the valve body inlet (A) and the valve core inlet (B) constitutes said valve inlet (17), and the valve core outlet at least partially forms said valve outlet (18),
        wherein the area of the overlapping portion of the valve body inlet (A) and the valve core inlet (B) changes as the valve core (16) rotates or slides, such that the area of the valve inlet (17) changes, to change the dynamic parameters of the fluid in the vascular simulation tube (4) over time, and
        wherein the valve core inlet (B) is one or more cross-shaped openings formed on the side wall.

* * * * *